United States Patent [19]

Lee et al.

[11] Patent Number: 5,208,392

[45] Date of Patent: May 4, 1993

[54] CATALYST AND METHOD FOR PREPARING MIXTURE OF CYCLOHEXANOL AND CYCLOHEXANONE

[75] Inventors: Kyu-Wan Lee; Ki-Won Jun; Eun-Kyung Shim, all of Daejeon, Rep. of Korea

[73] Assignee: Korea Research Institute of Chemical Technology, Daejeon, Rep. of Korea

[21] Appl. No.: 874,624

[22] Filed: Apr. 27, 1992

[30] Foreign Application Priority Data

Mar. 13, 1992 [KR] Rep. of Korea ............ 92-4140

[51] Int. Cl.⁵ .............. C07C 35/08; C07C 49/543
[52] U.S. Cl. .................... 568/836; 568/382; 568/383; 568/835
[58] Field of Search ............ 568/835, 836, 382, 383

[56] References Cited

U.S. PATENT DOCUMENTS

| | | | |
|---|---|---|---|
| 4,339,604 | 7/1982 | van Geem et al. | 568/836 |
| 4,341,907 | 7/1982 | Zelonka | 568/836 |
| 4,459,427 | 7/1984 | Middleton et al. | 568/836 |

Primary Examiner—Werren B. Lone
Attorney, Agent, or Firm—Thomas J. Dodd

[57] ABSTRACT

The present invention provides a novel Fe-Pd catalyst prepared by impregnating, either together or respectively, an iron source compound and a palladium source compound onto a carrier selected from the group consisting of silica, alumina and silica-alumina, and drying and calcining said Fe-Pd impregnated carrier in a flow of air or $H_2/N_2$; and a method for preparing a mixture of cyclohexanol and cyclohexanone by selectively oxidizing cyclohexane in a reaction medium provided with hydrogen and oxygen gases in the presence of said Fe-Pd catalyst.

10 Claims, No Drawings

CATALYST AND METHOD FOR PREPARING MIXTURE OF CYCLOHEXANOL AND CYCLOHEXANONE

FIELD OF THE INVENTION

The present invention relates to a catalyst for selective oxidation of cyclohexane and a method for preparing mixtures of cyclohexanol and cyclohexanone by selective oxidation of cyclohexane with said catalyst.

DESCRIPTION OF THE PRIOR ART

Aerated oxidation of cyclohexane is normally carried out in commercial processes in order to produce mixtures of cyclohexanol and cyclohexanone, which are commonly used, e.g., as important intermediates to the synthesis of nylon. However, such commercial processes have a number of common deficiencies, including the severe operating requirements of having to employ a high temperature, e.g., 150° C. or higher, and a high pressure, e.g., 8 atom or higher; and suffer from a very low yield, e.g., 4%. Further, the product selectivity is generally poor since the oxidation carried out under such severe conditions produces various decomposed oxides of cyclohexane. Accordingly, there has existed a need to develop a new process technology capable of ameliorating the severity of reaction conditions and improving the production selectivity of cyclohexanol and cyclohexanone.

Accordingly, various novel ideas have been proposed in search for the improved process technology. Specifically, the discovery that cytochrome P-450 oxidizes saturated hydrocarbons with substantially 100% selectivity in vivo has inspired the idea of utilizing a biological oxidation system in industrial processes.

For example, European Patent Publication No. 87,924 discloses a biomimetic process for oxidizing saturated hydrocarbons in a reaction system comprising an iron catalyst, hydrogen sulfide, acetic acid, pyridine solvent and oxygen, which uses chemicals difficult to be recovered and uneconomical.

Herron and Tolman have also disclosed a bimetallic oxidizing system of Fe-Pd/zeolite as an inorganic mimicry of cytochrome P-450. The catalytic ability of said oxidizing system is expected be a combination of the respective functions of two metal species: that is, that of palladium metal to convert hydrogen and oxygen to hydrogen peroxide; and that of iron to oxidize the produced hydrogen peroxide to hydroxylate hydrocarbon [J. Am. Chem., 109, 2836(1987)]. The Fe-Pd/zeolite catalyst has, however, proven to process a low activity as demonstrated by the production of less than one(1) molecule of product per one(1) iron atom.

SUMMARY OF THE INVENTION

Accordingly, the present invention provides a novel Fe-Pd catalyst prepared by impregnating, either together or separately, an iron source compound and a palladium source compound onto a carrier selected from the group consisting of silica, alumina and silica-alumina, and drying and calcining them in a flow of air or a mixture of $H_2/N_2$ gases. The catalyst so prepared and the oxidation process employing same for the production of a mixture of cyclohexanol and cyclohexanone is proven to be very effective and superior to prior art oxidation system, e.g., the catalytic process developed by Herron and Tolman. Unexpectedly, the present inventors have discovered that when a mixture of cyclohexanol and cyclohexanone is prepared by oxidizing cyclohexanone in a reaction medium provided with gases of hydrogen and oxygen in the presence of said novel Fe-Pd catalyst, the turnover ratio of the catalyst, based on iron, reaches about 13 and the yield is also much improved, even through the oxidation is carried out under a mild condition closed to normal pressure and temperature. Further, the improved oxidation process of the present invention entails very little traces of undesired oxides; and said catalyst can be readily recovered.

DETAILED DESCRIPTION OF THE INVENTION

The catalyst of the present invention employs oxidized iron such as $Fe^{2+}$ or $Fe^{3+}$ and oxidized palladium or palladium metal. Therefore, suitable iron source compounds include, for example, iron chlorides (e.g., iron(II) chloride and iron(III) chloride), iron sulfates (e.g., iron(II) sulfate and iron(III) sulfate) and iron nitrates(e.g., iron(II) nitrate and iron(III) nitrate). Representative palladium source compounds include: palladium chloride, palladium nitrate and palladium metal.

The carrier useful for the construction of the novel Fe-Pd catalyst system may be selected from the group consisting of silica, alumina and silica-alumina. Iron and palladium may be impregnated onto the carrier either together or separately.

The catalyst of the present invention is prepared by drying and calcining the Fe-Pd/carrier in a flow of air or a gaseous mixture of $H_2/N_2$. Said drying may be carried out at a temperature ranging from 100° C. to 150° C. for about 1 to 12 hours. The calcination may be carried out at a temperature between 300° C. and 600° C. for about 2 to 15 hours.

When said iron and palladium are impregnated onto the carrier separately, the iron/carrier may be basified with ammonia before the drying and the calcining steps.

The content of iron in the catalyst is preferably 0.1 to 10% by weight; and, the content of palladium is preferably 0.01 to 10% by weight. The ratio of iron and palladium is preferably within the range from 1:0.1 to 1:1 by weight.

In the reaction system employing the Fe-Pd catalyst of the present invention, palladium catalytically converts hydrogen and oxygen to hydrogen peroxide and, subsequently, iron helps oxidize said hydrogen peroxide to hydroxylate cyclohexane. The oxidation should be, therefore, carried out in a reaction medium provided with gases of hydrogen and oxygen.

The oxidation reaction may be preferably carried out in the presence of a reaction medium such as acetone. Acetone is most prefered as it evenly dissolves all reactants including hydrogen, oxygen, the produced hydrogen peroxide and cyclohexane so as to maximize their exposure and contact with the surface of the catalyst. In addition, acetone is inexpensive and can be recovered easily since it has a low boiling point.

Preferably, one part by weight of catalyst is used to oxidize 3 to 10 parts by weight of cyclohexane. Acetone may be used in an appropriate amount, preferably 10 to 40 times of the catalyst by weight. Hydrogen and oxygen gases may be respectively provided at a rate of between 0.5 and 10 parts by volume per minute to 1 part by volume of acetone.

The oxidation of the present invention may be carried out under a mild condition, e.g., at a atmospheric pressure and at a temperature ranging from 10° C. to 50° C. Further, the reaction time need not be longer then 16 hours.

The reactants evaporated during the reaction can be returned back to the reaction medium through the use of a refrigerated condenser.

The present invention is further illustrated by the following examples, which should not be taken to limit the scope of the invention.

The products after filtering out the catalyst are analyzed by gas chromatography using diisopropylbenzene as an internal standard. The yields are calculated by the following equations:

Yield of cyclohexanol (% by mole) =

$$\frac{\text{moles of the produced cyclohexanol}}{\text{moles of the starting cyclohexane}} \times 100$$

Yield of cyclohexanone (% by mole) =

$$\frac{\text{moles of the produced cyclohexanone}}{\text{moles of the starting cyclohexane}} \times 100$$

Total yield (% by mole) =

Yield of cyclohexanol (% by mole) +

Yield of cyclohexanone (% by mole)

EXAMPLE 1

To a solution of 1 g of $FeCl_2.4H_2O$ and 0.1 g of $PdCl_2$ in 15 ml of water was added 9 g of silica gel (Kiesel gel 60, surface area=426 $m^2/g$). The water was then evaporated off to impregnate iron and palladium onto the silica gel. The Fe-Pd/silica was dried at 150° C. for 2 hours and calcined at 400° C. for 3 hours in a flow of $N_2$ (96% by mole) and $H_2$ (4% by mole) gaseous mixture.

1 g of the catalyst so obtained was added to a solution of 5 g of cyclohexane in 20 ml of acetone; and, the reaction mixture was stirred at 30° C. under atmospheric pressure for 3 hours, bubbling gases of hydrogen and oxygen into the reation medium at the rate of 20 ml/min, respectively.

The yield of cyclohexanol was 2.87% by mole and the yield of cyclohexanone was 0.42% by mole. The total yield was 3.29% by mole.

EXAMPLE 2

To a solution of 1 g of $FeCl_2.4H_2O$ and 0.1 g of $PdCl_2$ in 15 ml of water was added 9 g of silica gel; and water was then evaporated off. The Fe-Pd/silica was dried at 150° C. for 2 hours in a flow of $N_2$ (96% by mole) and $H_2$ (4% by mole) gaseous mixture and calcined at 400° C. for 3 hours in a flow of air.

With 1 g of the catalyst so obtained, oxidation of cyclohexane was carried out in the same manner as in Example 1.

The yield of cyclohexanol was 2.27% by mole and the yield of cyclohexanone was 0.28% by mole, with the total yield of 2.55% by mole.

EXAMPLE 3

To a solution of 1 g of $FeCl_2.4H_2O$ and 0.1 g of $PdCl_2$ in 15 ml of water was added 9 g of silica gel; and water was then evaporated off. The remaining Fe-Pd/silica was dried at 150° C. for 2 hours and calcined at 400° C. for 3 hours in a flow of air.

With 1 g of the catalyst so obtained, oxidation of cyclohexane was carried out in the same manner as in Example 1.

The yield of cyclohexanol was 1.74% by mole and the yield of cyclohexanone was 0.21% by mole, with the total yield of 1.95% by mole.

EXAMPLE 4

To a solution of 1 g of $FeCl_2.4H_2O$ in 15 ml of water was added 9 g of silica gel; and water was then evaporated off. On the other hand, 9 g of silica gel to a solution of 0.1 g of $PdCl_2$ in 15 ml of water was added; and water was then evaporated off. Each of the Fe/silica and the Pd/silica was dried at 150° C. for 2 hours and calcined at 400° C. for 3 hours in a flow of a mixture of $N_2$ (96% by mole) and $H_2$ (4% by mole) gases.

With 1 g of the Fe/silica catalyst and 1 g of the Pd/silica catalyst so obtained, oxidation of cyclohexane was carried out in the same manner as in Example 1.

The yield of cyclohexanol was 3.78% by mole and the yield of cyclohexanone was 0.78% by mole, with the total yield of 4.53% by mole.

EXAMPLE 5

To a solution of 0.68 g of $FeCl_3.6H_2O$ in 15 ml of water was added 9 g of silica gel; and water was then evaporated off. On the other hand, 9 g of silica gel to a solution of 0.1 g of $PdCl_2$ in 15 ml of water was added; and water was then evaporated off. Each of the Fe/silica catalyst and the Pd/silica catalyst was dried at 150° C. for 2 hours and calcined at 400° C. for 3 hours in a flow of air.

With 1 g of each of the Fe/silica catalyst and the Pd/silica catalyst so obtained, oxidation of cyclohexane was carried out in the same manner as in Example 1.

The yield of cyclohexanol was 3.57% by mole and the yield of cyclohexanone was 0.23% by mole, with the total yield of 3.80% by mole.

EXAMPLE 6

To a solution of 0.34 g of $FeCl_3.6H_2O$ in 15 ml of water was added 9 g of silica gel; and water was then evaporated off. To the Fe/silica was added 0.425 g of aqueous ammonia solution and 10 g of distilled water so as to basify the catalyst. The solids were filtered and washed with 100 ml of distilled water. On the other hand, 9 g of silica gel was added to a solution of 0.1 g of $PdCl_2$ in water; and water was then evaporated off. Each of the Fe/silica catalyst and the Pd/silica catalyst was dried at 150° C. for 2 hours and calcined at 400° C. for 3 hours in a flow of air.

With 1 g of each of the Fe/silica catalyst and the Pd/silica catalyst so obtained, oxidation of cyclohexane was carried out in the same manner as in Example 1.

The yield of cyclohexanol was 2.51% by mole and the yield of cyclohexanone was 0.51% by mole, with the total yield of 3.02% by mole.

EXAMPLE 7

To a solution of 2.04 g of $Fe(NO_3)_3.9H_2O$ in 15 ml of water was added 9 g of silica gel; and water was then evaporated off. On the other hand, 9 g of silica gel was added to a solution of 0.1 g $PdCl_2$ in 15 ml of water; and water was then evaporated off. Each of the Fe/silica catalyst and the Pd/silica catalyst was dried at 150° C. for 2 hours and calcined at 400° C. for 3 hours in a flow of air.

With 1 g of each of the Fe/silica catalyst and the Pd/silica catalyst so obtained above, oxidation of cyclohexane was carried out in the same manner as in Example 1.

The yield of cyclohexanol was 1.58% by mole and the yield of cyclohexanone was 0.22% by mole, with the total yield of 1.80% by mole.

EXAMPLE 8

To a solution of 0.40 g of $FeSO_4 \cdot 7H_2O$ in 15 ml of water was added 9 g of silica gel; and water was then evaporated off. On to the other hand, 9 g of silica gel was added to a solution of 0.1 g $PdCl_2$ in 15 ml of water; and water was then evaporated off. Each of the Fe/silica catalyst and the Pd/silica catalyst was dried at 150°C. for 2 hours and calcined at 400° C. for 3 hours in a flow of air.

With 1 g of each of the Fe/silica catalyst and the Pd/silica catalyst so obtained above, oxidation of cyclohexane was carried out in the same manner as in Example 1.

The yield of cyclohexanol was 2.20% by mole and the yield of cyclohexanone was 0.32% by mole, with the total yield of 2.52% by mole.

EXAMPLES 9–10

The Fe-Pd catalyst prepared in Example 1 was used. Oxidation of cyclohexane was carried out in the same manner as in Example 1 except that the reaction temperatures were 40° C. and 50° C., respectively. The results are shown in Table 1.

TABLE 1

| Example No. | Reaction temperature | Yield (% by mole) | | |
|---|---|---|---|---|
| | | cyclohexanol | cyclohexanone | total |
| 9 | 40° C. | 3.94 | 0.53 | 4.47 |
| 10 | 50° C. | 0.76 | 0.09 | 0.85 |

EXAMPLES 11–13

The Fe-Pd catalyst prepared in Example was used. Oxidation of cyclohexane was carried out in the same manner as in Example 1 except that the amount of acetone was 10 ml, 30 ml and 40 ml, respectively; and, the reaction temperature was 40° C. The results are shown in Table 2.

TABLE 2

| Example No. | Amount of acetone (ml) | Yield (% by mole) | | |
|---|---|---|---|---|
| | | cyclohexanol | cyclohexanone | total |
| 11 | 10 | 2.21 | 0.29 | 2.50 |
| 12 | 30 | 2.65 | 0.43 | 3.08 |
| 13 | 40 | 2.68 | 0.44 | 3.09 |

EXAMPLES 14–15

The Fe-Pd catalyst prepared in Example 1 was used. Oxidation of cyclohexane was carried out in the same manner as in Example 1 except that hydrogen and oxygen gases were introduced at the rates of 10 ml/min and 30 ml/min, respectively; and, the reaction temperature was 40° C. The results are shown in Table 3.

TABLE 3

| Example No. | Inflow Rate (ml/min) | | Yield (% by mole) | | |
|---|---|---|---|---|---|
| | hydrogen | oxygen | cyclohexanol | cyclohexanone | total |
| 14 | 10 | 10 | 3.91 | 0.52 | 4.43 |
| 15 | 30 | 30 | 3.99 | 0.56 | 4.55 |

EXAMPLES 16–19

The Fe-Pd catalyst prepared in Example 1 was used. The oxidation of cyclohexane was carried out in the same manner as in Example 1 except that the reaction time was 1 hour, 7 hours, 12 hours and 17 hours, respectively. The results are shown in Table 4.

TABLE 4

| Example No. | Reaction time (hr) | Yield (% by mole) | | |
|---|---|---|---|---|
| | | cyclohexanol | cyclohexanone | total |
| 16 | 1 | 1.01 | 0.15 | 1.16 |
| 17 | 7 | 4.42 | 0.72 | 5.14 |
| 18 | 12 | 5.51 | 1.16 | 6.67 |
| 19 | 17 | 5.69 | 1.24 | 6.93 |

COMPARATIVE EXAMPLE 1

To a solution of 1 g of $FeCl_2 \cdot 4H_2O$ in 15 ml of water was added 9 g of silica gel; and water was then evaporated off. The Fe/silica was dried at 150° C. for 2 hours and calcined at 400° C. for 3 hours in a flow of $H_2$ (4% by mole) and $N_2$ (96% by mole) gaseous mixture.

With 1 g of Fe/silica catalyst so obtained, the oxidation of cyclohexane was carried out in the same manner as in Example 1.

It was observed that neither cyclohexanol nor cyclohexanol was produced.

COMPARATIVE EXAMPLE 2

To a solution of 0.1 g of $PdCl_2$ in 15 ml of water was added 9 g of silica gel; and water was then evaporated off. The Pd/silica was dried at 150° C. for 2 hours and calcined at 400° C. for 3 hours in a flow of $H_2$ (4% by mole) and $N_2$ (96% by mole) gaseous mixture.

With 1 g of Pd/silica catalyst so obtained, the oxidation of cyclohexane was carried out in the same manner as in Example 1, to find out that neither cyclohexanol nor cyclohexanone was produced.

COMPARATIVE EXAMPLE 3

Oxidation of cyclohexane was carried out in the presence of the same catalyst in the same manner as in Example 1 except that hydrogen gas was not introduced to find out that neither cyclohexanol nor cyclohexanone was produced.

COMPARATIVES EXAMPLE 4

Oxidation of cyclohexane was carried out in the presence of the same catalyst in the same manner as in Example 1 except that acetone was not used to find that the total yield of cyclohexanol and cyclohexanone was 0.01% by mole.

COMPARATIVE EXAMPLES 5–10

Oxidation of cyclohexane was carried out in the presence of the same catalyst and in the same manner as in Example 1 except that, instead of acetone, ethanol, isopropanol, methyl ethyl ketone, methyl isobutyl ketone, ethyl acetate and ethyl ether were used, respectively. The results are shown in Table 5.

TABLE 5

| Comparative Example No. | solvent | Yield (% by mole) | | |
|---|---|---|---|---|
| | | cyclohexanol | cyclohexane | total |
| 5 | ethanol | 0.52 | 0.12 | 0.64 |
| 6 | isopropanol | 0.56 | 0.10 | 0.66 |
| 7 | methyl ethyl ketone | 1.18 | 0.25 | 1.43 |
| 8 | methyl iso-butyl ketone | 1.13 | 0.19 | 0.32 |
| 9 | ethyl acetate | 0.43 | 0.23 | 0.66 |
| 10 | ethyl ether | 0.03 | <0.01 | 0.03 |

What is claimed is:

1. A method for preparing a mixture of cyclohexanol and cyclohexanone by selectively oxidizing cyclohexane at a temperature ranging from 10° to 50° C. in a reaction medium bubbled with hydrogen and oxygen gases in the presence of an iron-palladium catalyst prepared by impregnating, either together or separately, an iron salt compound and a palladium salt compound onto a carrier, followed by drying said impregnated carrier and calcining said dried carrier in a flow of air or a mixture of hydrogen and nitrogen gases, wherein the weight ratio of said cyclohexane to said catalyst is in the range of 3 to 10 and the weight ratio of said reaction medium to said catalyst is in the range of 10 to 40.

2. The method of claim 1 wherein said reaction medium is acetone.

3. The method of claim 1 wherein the hydrogen and the oxygen gases are provided at a respective rate ranging from 0.5 to 10 by volume per minute to 1 part by volume of the reaction medium.

4. The method of claim 1 wherein said iron salt compound is selected from the group consisting of iron chlorides, iron sulfates and iron nitrates.

5. The method of claim 1 wherein said palladium salt compound is selected from the group consisting of palladium chloride and palladium nitrate.

6. The method of claim 1 wherein the content of iron in said catalyst ranges from 0.1 to 10% by weight.

7. The method of claim 1 wherein the content of palladium in said catalyst ranges from 0.01 to 10% by weight.

8. The method of claim 1 wherein the ratio of iron and palladium in said catalyst ranges from 1:0.1 to 1:1 by weight.

9. The method of claim 1 wherein said drying is carried out at a temperature ranging from 100° C. to 150° C.

10. The method of claim 1 wherein said calcination is carried out at a temperature ranging from 300° C. to 600° C.

* * * * *